United States Patent [19]

Wilk

[11] Patent Number: 5,494,041
[45] Date of Patent: Feb. 27, 1996

[54] METHOD FOR USE IN SURGICAL OPERATION

[76] Inventor: Peter J. Wilk, 185 W. End Ave., New York, N.Y. 10023

[21] Appl. No.: 932,367

[22] Filed: Aug. 19, 1992

[51] Int. Cl.⁶ ................................................. G06F 159/00
[52] U.S. Cl. ................... 128/665; 128/653.1; 128/653.2; 604/284; 600/109
[58] Field of Search ..................... 364/413.13; 604/284, 604/286, 328, 22; 128/4, 5, 6, 653.1, 653.2, 898, 665; 340/706, 709, 705; 348/74; 382/6; 395/166

[56] References Cited

U.S. PATENT DOCUMENTS

| | | | |
|---|---|---|---|
| 4,742,815 | 5/1988 | Ninan et al. | 128/4 |
| 4,847,604 | 7/1989 | Doyle | 340/706 |
| 5,072,384 | 12/1991 | Doi et al. | 364/413.13 |
| 5,098,426 | 3/1992 | Sklar et al. | 606/5 |
| 5,183,471 | 2/1993 | Wilk | 604/284 |
| 5,195,541 | 3/1993 | Obenchain | 128/898 |
| 5,211,165 | 5/1993 | Dumoulin et al. | 128/653.1 |
| 5,215,521 | 6/1993 | Cochran et al. | 604/22 |
| 5,217,453 | 6/1993 | Wilk | 606/7 |

OTHER PUBLICATIONS

Digital Imaging, New Methods for Spotting Cancer, Coputers Software.

*Primary Examiner*—Gail O. Hayes
*Assistant Examiner*—Frantzy Poinvil
*Attorney, Agent, or Firm*—R. Neil Sudol; Henry D. Coleman

[57] ABSTRACT

A system for use in performing surgery comprises a video camera for generating a video signal encoding an image of organs of a patient, a display operatively connected to the video camera for displaying the image in response to the video signal, and an identification device operatively connected to the video camera for automatically analyzing the video signal to identify organs in the image. The identification device is operatively connected to the display for displaying symbols on the display to identify at least one of the organs in the image.

16 Claims, 1 Drawing Sheet

5,494,041

METHOD FOR USE IN SURGICAL OPERATION

BACKGROUND OF THE INVENTION

This invention relates to a method for use in surgery to facilitate the performance of surgical operations. This invention also related to an associated apparatus or system for use in the operating room to assist in the performance of surgical operations.

It is occasionally difficult in surgery, particularly laparoscopic surgery, to identify a patient's organs on a video screen. Sometimes, the organs are of unusual sizes and shapes which inhibits easy and quick identification.

In addition, accidents occasionally occur during operations which should be detected early to enable timely corrective measures. For example, during removal of the gall bladder in a laparoscopic operation, the gall bladder is grabbed with a laparoscopic grasping forceps to shift the organ in preparation for removal. Sometimes, the bladder is perforated by the grasping forceps, particularly when the bladder has thin walls. Bile then leaks from the perforated bladder into the abdominal cavity. If the perforation is detected early, it can be closed before the bladder empties of its charge of bile.

In another operative scenario, an intestine is nicked and the mucosal lining starts bubbling through the muscular wall of the intestine through the perforation. The perforation should be repaired as soon as possible to prevent faeces from leaking into the abdominal cavity.

In any case, the operating surgeon and his or her assistants are frequently too busy to quickly detect a perforation or other structural abnormality during the course of an operation.

OBJECTS OF THE INVENTION

An object of the present invention is to provide a method for use during surgery to facilitate the identification of a patient's organs.

Another object of the present invention is to provide a method for use during surgery to facilitate the detection of structural abnormalities such as perforations.

Another, more particular, object of the present invention is to provide such a method which is especially useful during laparoscopic surgery.

A further object of the present invention is to provide an apparatus or system for use in implementing a method in accordance with the invention.

Yet another particular object of the present invention is to provide such a method and/or apparatus which may be called into use easily and quickly, on an optional basis, during surgery.

These and other objects of the invention will be apparent from the descriptions and illustrations provided herein.

SUMMARY OF THE INVENTION

A system for use in performing surgery comprises, in accordance with the present invention, a video camera for generating a video signal encoding an image of organs of a patient, a display operatively connected to the video camera for displaying the image in response to the video signal, and an identification device operatively connected to the video camera for automatically analyzing the video signal to identify organs in the image. The identification device is operatively connected to the display for displaying symbols on the display to identify at least one of the organs in the image.

Preferably, the identification device includes a computer and a video mixer. Pursuant to another feature of the present invention, the computer is programmed to identify abnormal structural conditions of the organs and to provide an alert signal upon detecting any one of the abnormal conditions. The detectable abnormal conditions include such structural irregularities such as perforations of the organs. Where a perforation results in leaking fluid, the computer may be programmed to detect a fluid stream. Where a perforation results in a bubble of a mucosal membrane, for example, where an intestinal wall is cut, the computer is programmed to recognize bubbles of a predetermined specific size range.

Pursuant to another feature of the present invention, the system further comprises a selector operatively connected to the identification device for inducing that device to display the symbols on the display. Accordingly, during a surgical operation, a video screen in the operating room normally presents an image as it is transmitted from the video camera. However, upon the generation of an enabling signal, for example, in response to the pressing of a keyboard button, the computer transmits symbol encoding signals to the video mixer for inducing the incorporation of the symbols into the video image. The symbols may include the names of the identified organs, as well as lead lines and/or highlighting outlines for the organs. The hightlighting may be done in different colors to facilitate differentiation between the different organs.

A video identification system in accordance with the present invention is especially suited for use in laparoscopic surgery. In that event, the video camera is provided in a laparoscope assembly.

A method for use in performing surgery comprises, in accordance with the present invention, the steps of (a) generating a video signal encoding an image of organs of a patient, (b) displaying the image in response to the video signal, (c) automatically analyzing the video signal to identify organs in the image, and (d) displaying identification symbols on a video display to identify at least one of the organs in the image.

Pursuant to another feature of the present invention, the step of analyzing the video signal includes the steps of operating a computer to identify organs in the image and operating a video mixer connected to the computer to mix in a video identification signal from the computer with the video signal encoding the image of the patient's organs.

Pursuant to another feature of the present invention, the method further comprises the step of signaling the computer to display the identification signals. In this case, the display of the identificatiion symbols is implemented only upon request of the surgeon or other operating room personnel.

As discussed above, the displayed symbols preferably include names for the organs. Alternatively, the surgeon or an assistant may instruct the computer to hightlight a specific organ. Upon a request, for example, to indicate the cystic duct, the computer may generate an arrow pointing to an image of the duct on the video monitor, with or without the words "cystic duct." Alternatively, the cystic duct may be highlighted, for example, by a line around the contour of the organ, or by imparting a different color to the image of the duct on the video monitor.

Pursuant to another feature of the present invention, the method further comprises the steps of automatically identifying abnormal structural conditions of the organs and providing an alert signal upon detecting any one of the abnormal conditions. This feature is particularly advantageous where there is a substantial amount of activity at the surgical site and accordingly where the surgeon's attention is simultaneously drawn by many competing objects and actions. The computer thus automatically monitors the video signal for such abnormal conditions as bile leaking from the gall bladder or mucosal membrane bubbles appearing on the colon. If necessary, several video cameras may be aimed at or about the surgical site. Although the surgeon may be able to monitor only one image to any appreciable extent, the computer can effectively police all video images to detect any irregularities which might result in a serious complication.

The method is particularly effective in assisting during laparoscopic surgery.

DETAILED DESCRIPTION

Figure 1:
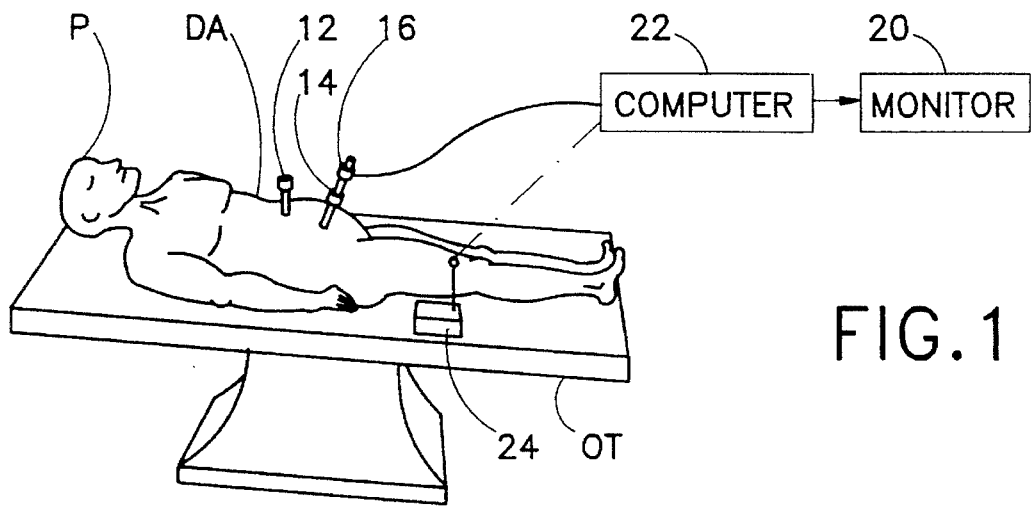
FIG. 1 is partially a schematic perspective view and partially a block diagram showing components of a video identification and detection system for assisting surgeons during surgical operations.

As illustrated in FIG. 1, a patient P on an operating room table OT has a distended abdomen DA which has been insufflated with carbon dioxide gas in a conventional procedure involving the disposition of trocar sleeves 12 and 14 in the abdominal wall. Laparoscopic instruments including a laparoscope 16 pass through the trocar sleeves to become partially inserted into the abdominal cavity of the patient P.

A video camera 18 (FIG. 2) in laparoscope 16 is operatively connected to a video monitor 20 via a computer 22. Computer 22 automatically analyzes the video signal from camera 18 to identify organs of the patient in the image carried by the camera-generated video signal. In response to activating signals from a peripheral input device 24, computer modifies the video signal to incorporate organ-identifying symbols in the video signal.

Figure 3:
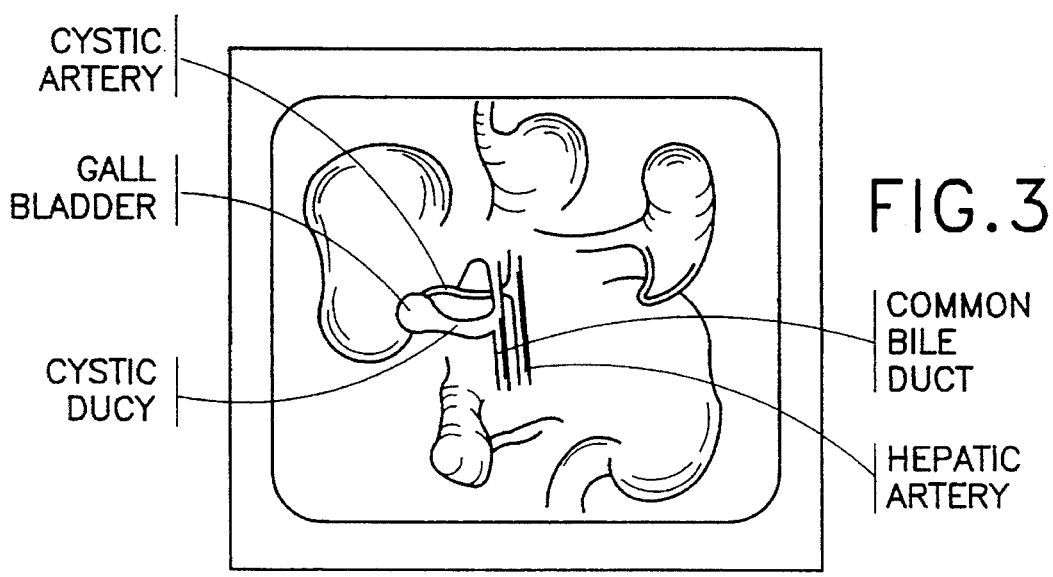
FIG. 3 is a diagram of a video screen showing images of organs and computer generating identifying symbols in accordance with the present invention.

As illustrated in FIG. 3, the symbols may take the form of common names for the various organs. FIG. 3 particularly shows the gall bladder, the cystic duct, the common bile duct, the cystic artery and the hepatic artery, together with their names and lead lines, for use in a laparoscopic colecystectomy operation. The organ names are superimposed over the video image from video camera 18 and may be in a different color to facilitate distinguishing the names and the lead lines from the organs and tissues shown in the image.

Other, alternative or supplemental, techniques for identifying the organs include outlining the organs or modifying the contrast or color of the organs of interest. The outlines or colors applied to the organs may be different to facilitate visual differentiation. In any event, a plurality of organs should remain in view on screen to enable an appreciation of relative organ locations and structures.

Figure 2:
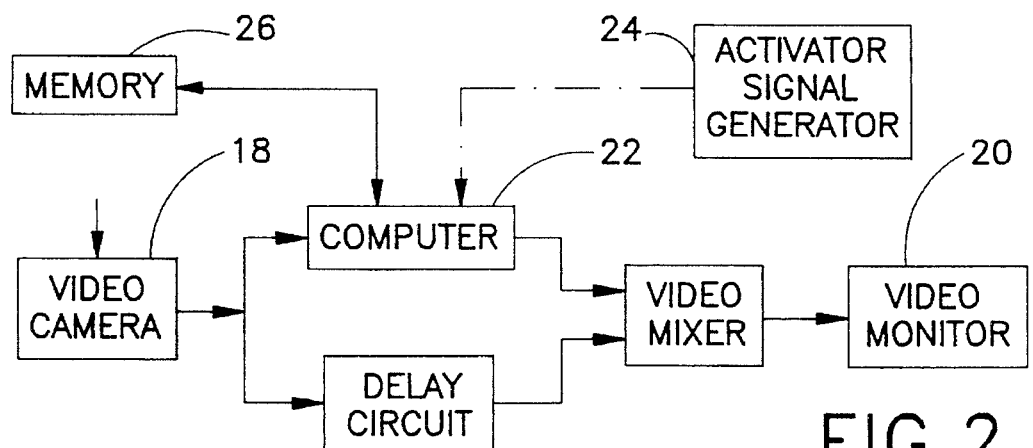
FIG. 2 is a block diagram showing components of the system of FIG. 1.

As illustrated in FIG. 2, computer 22 is connected to a memory 26 for comparing the images encoded in the incoming video signals with encoded shapes, textures and relative locations of organs in memory 26. Computer 22 is thereby able to automatically distinguish different organs.

As further illustrated in FIG. 2, computer 22 is operatively connected at an output to a video mixer 28. Video mixer 28 is also connected at an input to video camera 18 for receiving therefrom the video image of the patient's internal organs, as obtained via laparoscope 16. Video mixer 28 is connected to camera 18 via a delay circuit 30, whereby computer 22 is provided with sufficient time to analyze the incoming video signals for organ identification.

It is to be noted that input device 24 for generating an identification process activation signal may be connected to computer 22 via a lead 32 (FIG. 2) or, alternatively, a wireless communications link 34 (FIG. 1). Wireless link 34 is advantageous in that it serves to reduce the clutter in the operating room.

It is to be also noted that input device 24 may be configured for enabling a user to inform computer 22 as to which organs or which groups of organs it is desired that the computer identify. For example, during a colecystectomy operation, a request may be made to identify or hightlight only one organ such as the cystic duct, or a limited plurality of organs such as the cystic duct and the cystic artery (see FIG. 3).

Computer 22 may be additionally programmed to identify abnormal structural conditions of the patient's organs and to provide an alert signal upon detecting any one of the abnormal conditions. The alert signal may take the form of an audio signal, for example, or a flashing indication on a video monitor. Detectable abnormal conditions include such structural irregularities such as perforations of the organs. Computer 22 may be programmed, for example, to detect a fluid stream such as bile leaking from the gall bladder. In addition, or alternatively, computer 22 may be programmed to recognize a bubble of a mucosal membrane, for example, where an intestinal wall is cut. Such bubbles will occur on the intestine and will have a size limitation.

Early detection of perforations and other structural abnormalities facilitates timely execution of corrective measures. The surgical procedure may be interrupted to perform necessary repairs.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for use in performing surgery, comprising the steps of:

disposing a laparoscopic trocar sleeve in a skin surface of a patient;

inserting at least a portion of a laparoscopic video camera device through said trocar sleeve and at least partially into the patient;

upon insertion of said camera device through said trocar sleeve, operating said camera device to generate a video signal encoding video data pertaining to internal organs of the patient;

displaying on a display a video image of said organs in response to said signal;

automatically analyzing said signal to identify organs in said image; and while maintaining at least a substantial portion of said image on said display, displaying identification symbols on said display, in overlap with a portion of said image, to identify at least one of the organs in said image.

2. The method defined in claim 1 wherein said step of analyzing includes the steps of operating a computer to identify organs in said image and operating a video mixer connected to said computer to mix in a video identification signal from said computer with the video signal encoding the image of the patient's organs.

3. The method defined in claim 2, further comprising the step of signaling said computer to display said identification symbols.

4. The method defined in claim 1 wherein said symbols include a name for said one of said organs.

5. The method defined in claim 1, further comprising the steps of automatically identifying abnormal structural conditions of said organs and providing an alert signal upon detecting any one of said abnormal conditions.

6. The method defined in claim 5 wherein said abnormal conditions include perforations of said organs.

7. The method defined in claim 5 wherein said abnormal conditions include a perforation resulting in leaking fluid.

8. The method defined in claim 5 wherein said abnormal conditions include a perforation resulting in a bubble of a mucosal membrane.

9. The method defined in claim 1, further comprising the step of performing a laparoscopic surgical operation on the patient, said steps of operating, displaying said image, analyzing, and displaying identification symbols being executed during said operation,, whereby said steps of generating, displaying said image, analyzing, and displaying said identification symbols are performed in real time.

10. The method defined in claim 1 wherein said step of automatically analyzing includes the step of operating a computer to identify organs in said image.

11. A method for use in performing surgery, comprising the steps of:

disposing a laparoscopic trocar sleeve in a skin surface of a patient;

inserting at least a portion of a laparoscopic video camera device through said trocar sleeve and at least partially into the patient;

upon insertion of said camera device through said trocar sleeve, operating said camera device to generate a video signal encoding video data pertaining to internal organs of the patient;

displaying on a display a video image of said organs in response to said signal;

automatically analyzing said signal to detect an abnormal structural condition of said organs; and while maintaining at least a substantial portion of said image on said display, displaying an identification symbol on said display, in overlap with a portion of said image, to indicate a location of the detected abnormal condition.

12. The method defined in claim 11 wherein said abnormal condition is a perforation of any one of said organs.

13. The method defined in claim 11 wherein said abnormal condition is an organic perforation with leaking fluid.

14. The method defined in claim 11 wherein said abnormal condition includes a bubble of a mucosal membrane.

15. The method defined in claim 11, further comprising the step of performing a laparoscopic surgical operation on the patient, said steps of operating, displaying, analyzing and providing being executed during said operation, whereby said steps of generating, displaying, analyzing and providing are performed in real time.

16. The method defined in claim 11 wherein said step of automatically analyzing includes the step of operating a computer to identify organs in said image.

* * * * *